United States Patent [19]

Onik et al.

[11] Patent Number: 4,583,538
[45] Date of Patent: Apr. 22, 1986

[54] METHOD AND APPARATUS FOR STEREOTAXIC PLACEMENT OF PROBES IN THE BODY UTILIZING CT SCANNER LOCALIZATION

[76] Inventors: Gary M. Onik, 1129 Judah, San Francisco, Calif. 94122; Eric R. Cosman, 872 Concord Ave., Belmont, Mass. 02178; Trent H. Wells, 8151 San Carlos Ave., So. Gate, Calif. 90280

[21] Appl. No.: 607,175

[22] Filed: May 4, 1984

[51] Int. Cl.$^4$ .............................................. A61B 19/00
[52] U.S. Cl. ................................. 128/303 B; 128/653; 378/20
[58] Field of Search .................... 128/303 B, 659, 653, 128/660, 630; 378/20, 207, 99

[56] References Cited

U.S. PATENT DOCUMENTS

| | | | |
|---|---|---|---|
| 3,881,110 | 4/1975 | Hounsfield et al. | 378/20 |
| 4,058,114 | 11/1977 | Soldner | 128/303 B |
| 4,233,507 | 11/1980 | Volz | 378/20 |
| 4,341,220 | 7/1982 | Perry | 128/303 B |
| 4,360,028 | 11/1982 | Barbier et al. | 128/303 B |
| 4,400,819 | 8/1983 | Bens et al. | 378/20 |

OTHER PUBLICATIONS

Bergstrom et al, "Stereotaxic Computed Tomography", Am. J. Roentgenol 127: 167-170, 1976.
Norman et al, "Localizatin With the EMI Scanner", Dec. 1975, pp. 961-964.

Primary Examiner—Kyle L. Howell
Assistant Examiner—Ruth S. Smith
Attorney, Agent, or Firm—Richard J. Birch

[57] ABSTRACT

The method and apparatus are presented which allow for CT guided biopsies of the body. The method is based on the finding of a reference point on the patient's body that exactly correlates to a point on the CT scan. This is accomplished by means of a localization device placed on the patient's skin which can be identified in cross section on the CT scan. Measurements of the localization device on CT scan can then be correlated to the device on the patient.

12 Claims, 15 Drawing Figures

METHOD AND APPARATUS FOR STEREOTAXIC PLACEMENT OF PROBES IN THE BODY UTILIZING CT SCANNER LOCALIZATION

BACKGROUND OF THE INVENTION

With the advent of third and fourth generation CT scanners, invasive and interventive procedures that are performed under CT guidance are now used extensively. CT guided needle aspiration biopsies have been highly successful and have alleviated the need for diagnostic surgery in the vast majority of cases: (Haaga J., Lipuma J., Bryon P., Balsara V., Cohn A., Clinical comparison of small and large caliber cutting needles for biopsy. Radiology 164:665–667, March 1983; Mulari Sunduram, et al., Utility of CT guided abdominal aspiration procedures. AJR 139:1111–1115, December 1982; Harvey M. Goldstein, et al., Percutaneous fine needle aspiration biopsy of pancreatic and other abdominal masses. Radiology 123:319–322, May 1977; and Robert Isler, et al., Tissue core biopsy of abdominal tumors with a 22 gauge cutting needle. AJR 136:725–728, April 1981). In addition, CT now guides the drainage of abdominal abcesses by way of a percutaneous route eliminating the need for repeat surgery. At the present time, however, all of these procedures are guided by hand, consequently it is usually a time-consuming process that requires multiple needle manipulations with repeat scanning to verify the position of the needle. Because of this lack of proper instrumentation, it can take as long as an hour to biopsy a 2–3 cm lesion in the liver of a patient.

CT stereotaxis is a well established procedure for the head (Brown, R. A., A computerized tomography-computer graphics approach to stereotaxic localization. J. Neurosurg., 50:715–720, 1979; Brown, R. A., A stereotactic head frame for use with CT body scanners. Invest. Radiol., 14:300, 1979; Brown, R. A., Roberts, T. S., Osborn, A. G., Stereotaxic frame and computer software for CT-directed neurosurgical localization. Invest. Radiol., 15:308–312, 1980; and Roberts, T. S., Brown, R. A., Technical and clinical aspects of CT-directed stereotaxis. Applied Neurophysiology, 43:170–171, 1980). The brain, because of its consistent relationship to the boney skull, can have a rigid frame attached to it which can then provide the needed reference coordinates from which various paths can be calculated. It should be noted that in all of the present stereotaxic devices for the brain, the reference coordinates are taken from the attached frame not the patient's skin and referenced to the target. The body, however, does not have the constant relationships of its surface anatomy to the underlying organs. In addition, there is no structure to which a rigid frame can be attached. To add to the difficulties, many of the organs within the abdominal cavity move with respiration so that with the changes in the phase of respiration, the relationship of the organs to the surface are different. It is for these reasons that at present there has been no published attempt to use CT stereotaxis in the guiding of probes or needle into the neck, chest, abdomen, pelvis, and extremities.

BRIEF DESCRIPTION OF THE INVENTION

The present invention relates to a method and an apparatus to achieve precist CT stereotaxic placement of probes anywhere in the body from images on a CT scanning machine (x-ray, NMR, P.E.T., etc.). The invention utilizes the technique of finding a reference point in the patient's body that exactly correlates to a point on the CT scan. The reference point is established by means of a localization device that is placed on the skin of the patient. The localization device is identified in cross-section on the CT scan. Measurements of the localization device on the CT scan are then correlated to the device on the patient.

In addition to the general object of providing a method and apparatus for allowing CT guided biopsies of the body, the present invention has the following subsidiary objects and features:

(1) Use of a method for calculating multiple angled approaches from the reference point;

(2) Use of a stereotaxic frame upon which the angles calculated can be set and which will guide the probes to the target, the frame either being attached to the CT table, or patient, or CT independent by mounting to the floor;

(3) Use of a respirator gating device which will allow all scans and the biopsy to be obtained in the same phase of respiration;

(4) Use of an immobilization device which comprises a vacuum bag filled with plastic beads which molds to the patient's body; and, (5) Use of a circular level or leveling systems on various axes attached to the immobilization device which allows for repositioning the patient outside the CT scanner making the CT biopsy scanner-independent;

(6) Use of a localizer device attached to the skin to determine a reference point on the body;

(7) Use of a quick-release needle guide device for fast sequential placement of probes in the body.

BRIEF DESCRIPTION OF THE FIGURES

These objects and other objects and features of the invention will best be understood from a detailed description of a preferred embodiment of the invention selected for purposes of illustration and shown in the accompanying drawings in which:

FIGS. 8A and 8B depict in perspective and plane view, respectively, a leveling device for attaching to the patient or board to relocate the patient out of the scanner; and, FIGS. 9A, 9B and 9C are views in perspective of quick-release needle guide systems.

DESCRIPTION OF THE METHOD

The present description relates to a new method and devices that allow identification of a reference point on a CT scan and then allow identification of that point on the patient's skin. From the point on the patient's skin, any point of entry on the patient's skin can then be calculated. From the CT scan, the coordinates of a target point can then be identified. Using mathematical calculations, the path length and angles needed to reach that target from the skin entry point can then be calculated. A biopsy guide oriented in the plane of the CT scan can then have the calculated angles set upon it which will aim the probe at the identified skin entry point from which the target coordinates will be reached.

Figure 1:
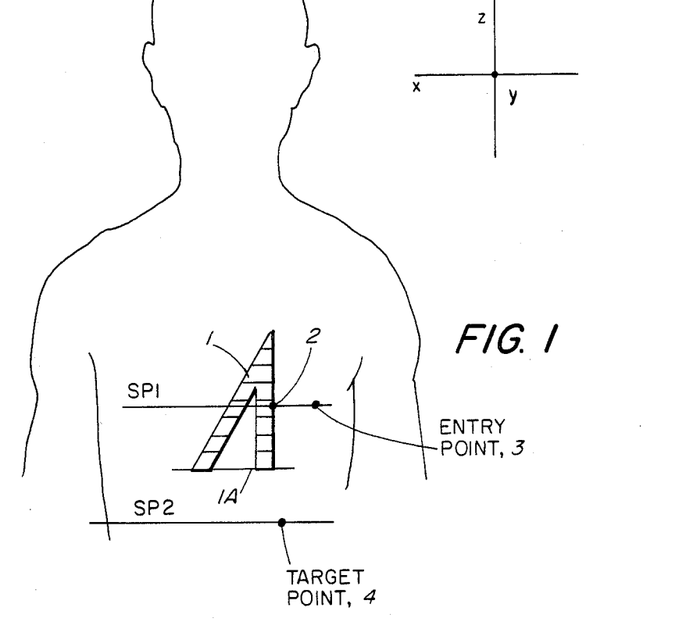
FIG. 1 is a diagrammatic view showing a localization device placed on a patient's skin with its base oriented in the axial plane (x axis)
Figure 2:
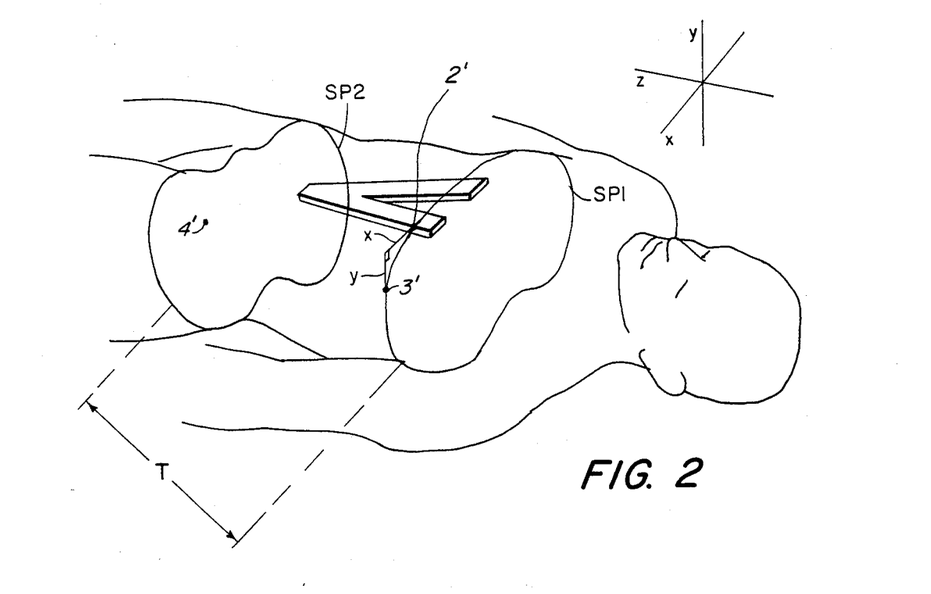
FIG. 2 is a three-dimensional view of the localization device as it relates to two different axial sections in a series of CT slices.

FIG. 1 illustrates the localization device 1 placed on the patient's body as viewed from above. The base 1A of the device is oriented along the x axis parallel to the plane in which the axial sections of the CT scan will be obtained. SP1 is the scan plane from which the reference point 2 and the skin entry point 3 will be obtained. SP2 is the scan plane from which the target point 4 will be identified. FIG. 2 shows in three dimensions the two scan planes through which the CT scans will be obtained of the patient's body. Point 2' is the reference point obtained from the localization device. Point 3' is the skine entry point that was obtained by moving calculated distances from the reference point 2'. Point 4' is the target point whose coordinates were obtained from the CT scan. The distance marked T is the distance along the z axis between the two scan planes. The distances marked x and y are the distances needed to be traveled along the x axis and y axis to get from the reference point 2' to entry point 3' on the patient's skin.

It is understood that the surgeon can decide to use the point 2' itself as the entry point through which the instrument will pass to a target. Thus, it may be that point 3" 'coincides' with point 2". This simply means that $X' = Y' = 0$. In the same way, referring to FIG. 2, it may be that target 4' is actually in the scan plane SP1. Thus, the reference to the first and second tomographic cuts coinciding is merely that SP2 is equal to SP1, i.e., the entry point and target point are in the same axial scan.

The localizer device 1 in FIG. 1 is shown as a triangle with base 1A, but other shapes or device types can be used to do the same localization. The present invention is not intended to be limited to any particular form or shape of localizer device 1. The device can be made of various materials such as plastic, carbon fiber, etc. and be solid, hollow, or of tubular construction.

Figure 3A:
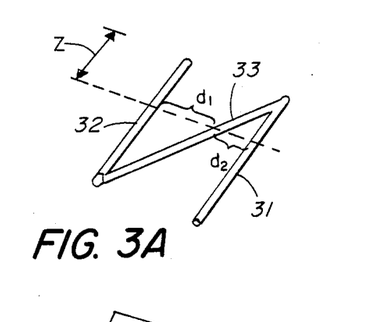
FIGS. 3A through 3D depict various types of localizer devices that can be placed on the patient to determine a reference point on the patient's skin from CT images.
Figure 3B:
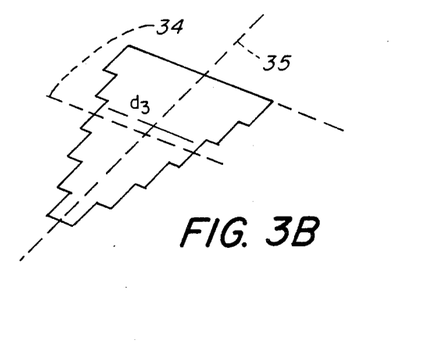
Figures 3C, 3D:
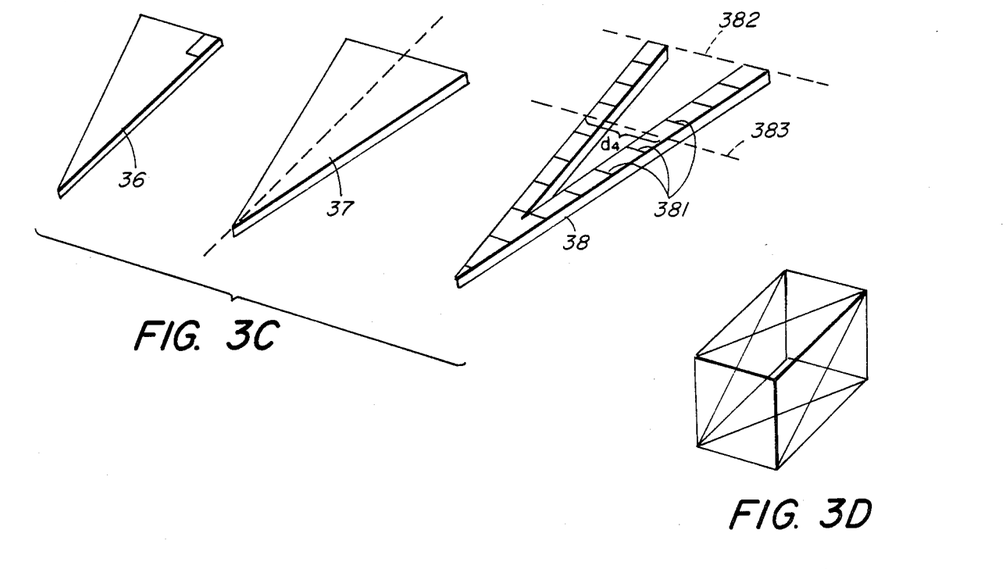

FIGS. 3A through 3D illustrate other types of localizer devices. In FIG. 3A, an "N"-type structure consists of parallel rods 31 and 32 and a diagonal 32 such that if the CT cuts the device and the CT axis is aligned parallel to 31 or 32, then the ratio of distances $d_1/d_2$ can be related to the z distance from the devices end, thus giving information on the location of the scan plane in real space. The rods can be made of carbon fiber so as to show up on the CT image as spots. FIG. 3B shows a stepped triangle localizer, where if axis 34 is aligned before the scan to be parallel to the scan, then the distance $d_3$ as measured on the scan compared to the real localizer will give the position of the scan cut along the axis 35 (z-axis). In FIG. 3C, right triangles 36, isoceles 37, and hollow triangle 38 all are useful examples of localizers. Note in triangle 38 there are lines 381 on it which are parallel to base line 382, which can be aligned with the CT plane prior to scanning. Now if a certain distance $d_4$ is seen on the CT scan corresponding to a cut line 383 through 38, then this can be quickly located on 38 by the lines 381. If the lines are placed such that $d_4$ is an integral value across 38, then one needs only to interpolate to get the position of 383. Note, too, that any intersection of 383 with the four edges of 38 will serve as a reference skin point (viz 2 of FIG. 1). By making 38 i.e., open in the center hollow as shown, it may be flat on the patient's body and roughly independent of the curvature of the skin under it. Localizer device 38 can have a sticky underside so that it is quickly stuck to or removed from the patient and may be served sterile-packed and disposable.

Box structures with more diagonals and rods as in FIG. 3D can be used and attached to the patient to determine the entire plane of CT cut, even for oblique planes or when no prior alignment is utilized. Intersection of all the rods and diagonals determines an arbitrary scan plane. Note that it is useful to align an edge or surface of these localizers to the scan plane before scanning to simplify the localizer identification. This is not essential, however, since, for example, sequential scan across a triangle, as FIG. 3A, 3B, 3C, can lead to determination of the scan cut without prior alignment. Once the localizer is attached to the skin or body, then scanning allows a point to be identified on the patient's skin which is related to a corresponding point on the localizer.

Figure 4:
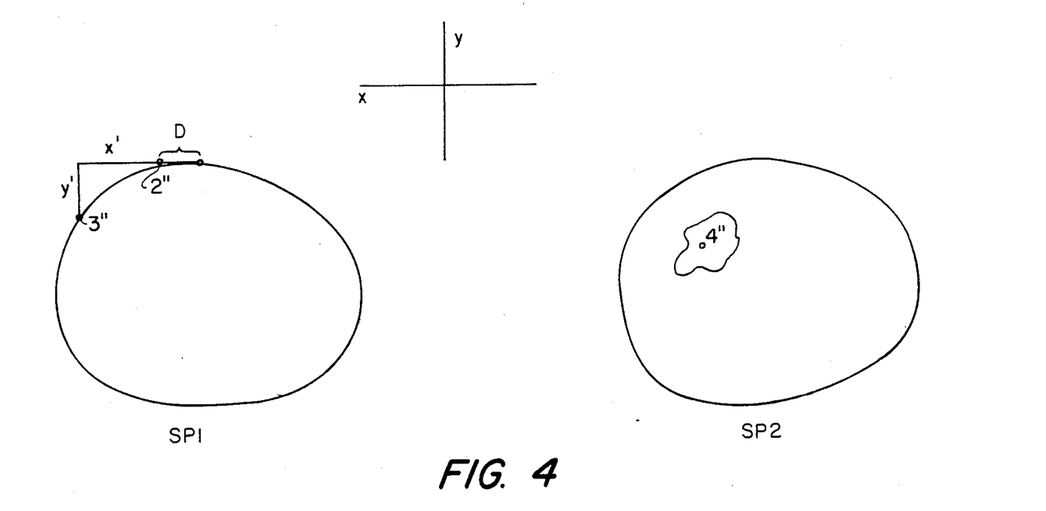
FIG. 4 shows a two-dimensional representation of the two axial sections of FIG. 2 with reference made to the fiducial reference point as defined by the localization device, as well as the skin entry point and the target point.

FIG. 4 shows axial CT slices through the previously noted planes which are again labeled on the diagram SP1 and SP2. The scan slice marked SP1 shows the cross sectional distance of the localization device labeled D. The lateral margin of the cross section of the localization device defines point 2" which can be related back to point 2' that was previously identified on the patient in FIG. 2. Point 3" is the entry point as viewed on the CT scan. The distances x' and y' are the calculated distances on the CT scan that relate point 2" to point 3" and which correlate to the distances marked x and y in FIG. 2. Point 4" as noted on SP2 is the target point on the CT scan that relates to point 4' as seen in FIG. 2. It can be seen that by measuring the distance D on the CT scan, and by then measuring that same distance on the localization device on the patient, that the point that is defined as 2" on the CT scan can then be directly found on the patient previously defined as point 2'. All calculations then made from point 2" in FIG. 2 and point 2 in FIG. 1 on the CT scan can then be made from point 2' on the patient's body.

Figure 5:
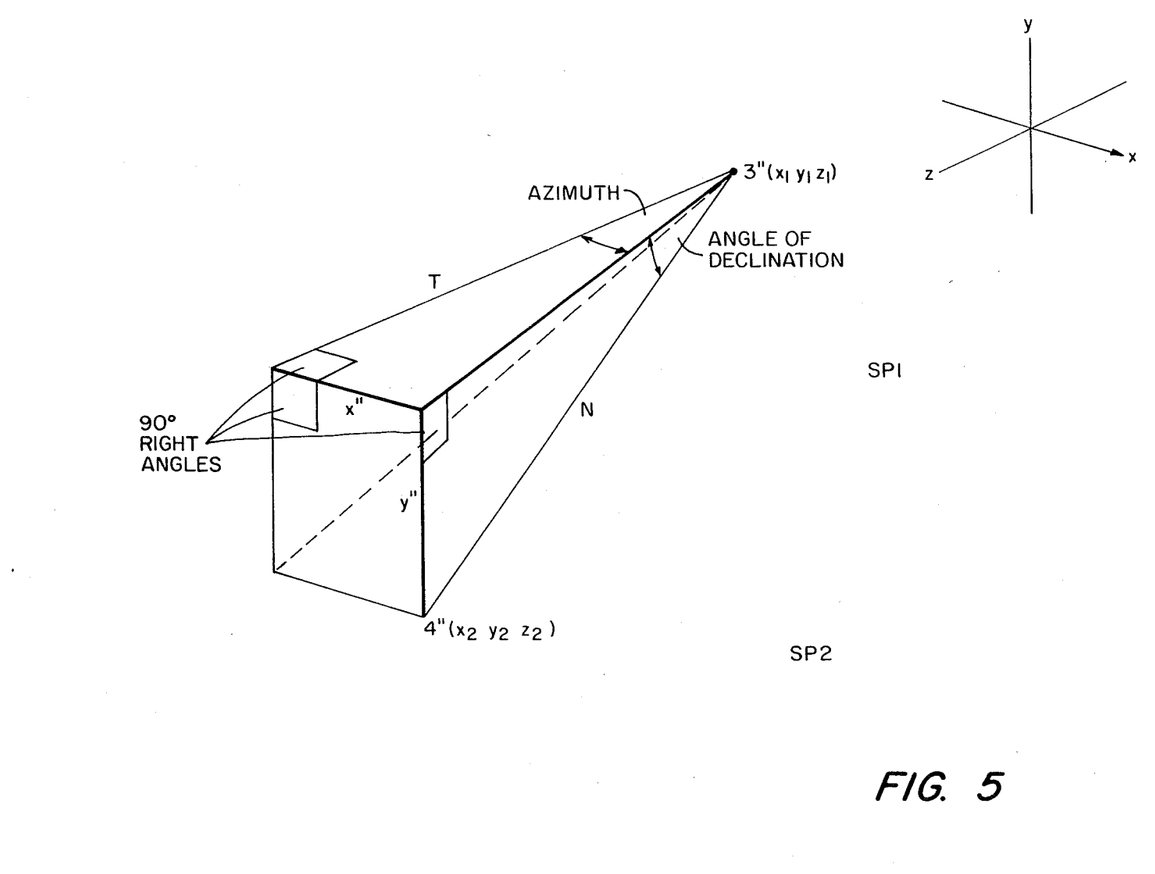
FIG. 5 shows the three-dimensional calculations employed for the definition of oblique compound angle needle or probe paths.

FIG. 5 shows point 3" with coordinates $x_1, y_1, z_1$ as the needle entry point and point 4" with coordinates $x_2, y_2, z_2$, as the target coordinates. It can be seen that by knowing the x" and y" as well as the distance T (all distances that can be calculated from the cT scan and the scanning parameters), the azimuth, the angle of declination, and the needle path length N can be calculated.

Figure 6:
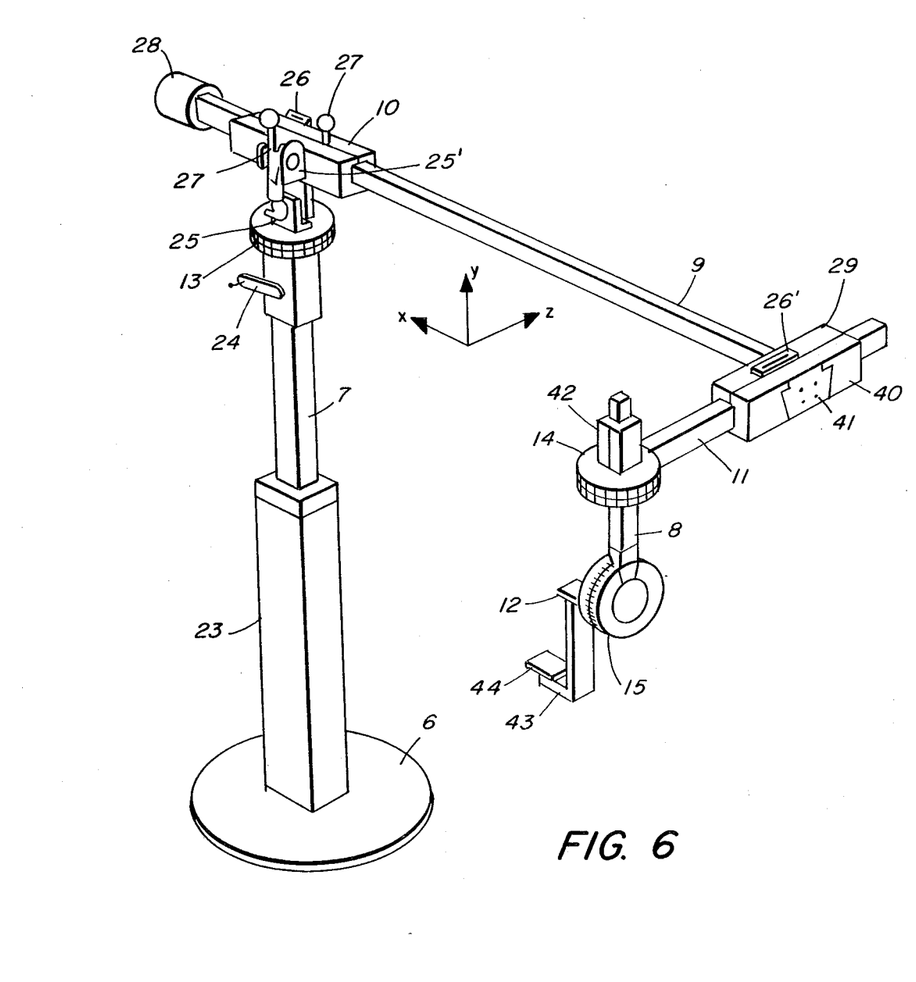
FIG. 6 is a view in perspective of a biopsy guide that holds the needles or probes and upon which is set the calculated angles.

FIG. 6 shows a stereotaxis guide instrument that can be used to guide the needle or probe on the calculated course. In this version, the guide is independent of the CT scanner or its table. The base 6 is placed on the floor and has no connection to the CT table. The guide has two moving members that provide displacements in the y-axis direction; a main vertical post 7 and a smaller vertical bar 8. X-axis movement is accomplished by an x-travel bar 9, through its guide yoke 10. Z-axis movement is accomplished by movement of a z-bar 11. By these x,y,z movements, the tip of a needle in needle holder 12 can be brought to the exact entry point of the skin for any settings of the angular rotation members of the device. Although two y-bars are shown, a single y-bar is also workable.

Angular rotations about these axes enable any orientation of the needle direction to be set for penetration to hit the target. Bearing 13 enables x-bar 9 to be swung over the patient and 9 to be aligned parallel to the scan plane. Bearing 14 provides, thereafter, the calculated azimuth angle to be set, and bearing 15 enables the declination angle to be set. Thus, once 13 is aligned, 14 and 15 are set according to the calculated angles of FIG. 4, and the x,y,z translations made to set the probe tip to the body entry point 2'. Advancing the needle by calculated distance N then enables the tip to just reach target 4' in the body.

The stereotaxis guide instrument of FIG. 6 has specific advantages and details. Thus, having base 6 on the floor makes it free of the CT table, and therefore scanner independent. One does not have to modify or adapt each table to hold the frame. Furthermore, it eliminates any complexity of equipment which must be attached to the table or patient. Base 6 can have a vacuum seal to the floor so that it is easily put in place or removed; or placed on either side of the CT or operating table. The first vertical (or y) travel is column 7, which moves in and out of column 23, so that the overall height of x-bar 9 may be adjusted to suit the table height. This is done by turning crank 24 which activates an internal gear system to raise or lower 7. First aximuth (or O) bearing 13 has an angle dial on it and enables arm 9 to be swung over the patient, or out of the way altogether, with ease. The index and set stop on it enable easy alignment of bar 9 over the patient and CT table so that bar 9 can be set up and aligned initially to the CT plane. This can be important for quick alignment on the CT or operating tables. Vertical bearing 25 allows 9 to swing up or down, for alignment to the horizontal. A level or bubble gauge 26 makes this step easily done. Adjustment vernier 27 enable this angle to be fine-tuned.

A second vertical bearing 25' allows z-bar 11 to be adjusted to be in the horizontal or x-z plane defined by the scanner axes. Bearings 25 and 25' can be replaced by a single ball type bearing with vernier screws to achieve the same alignment of 9 and 11 to horizontal as is done in a surveying transit. A level 26' checks the z-bar level. Arm 9 travels in block 10, and set-stop 27 can clamp a position. A scale on 9 enables exact x-movements to be measured, and roller bearings inside 10 can make the movement of the bar more frictionless, for ease of handling. Counter-weight 28 balances the arm 9. End block 29 has similar bearings for ease of bar 11 travel in the Z direction. End block 40 and attachment 41 of bar 9 enable that 11 can be reversed on the Z direction, so that the instrument can be set on either side of the patient. Bar 11 is graduated for exact Z motion. A second aximuth bearing 14 makes quick setting of the azimuth angle in FIG. 5 possible, and it is graduated in degrees for direct setting of calculated angles. Bearing 42 allows second vertical (or y) travel bar 8 to move easily and be set in an exact y-position. This second vertical bar enables the probe carrier 12 to be brought down close to the body, making possible oblique out-of-CT plane approaches with ease. End bearing 15 is the declination angle of FIG. 5, and is graduated in degrees to enable setting calculated angles of approach. An extension of the electrode carrier 43 can enable the quick-release needle guide 44 to be brought very close to the skin to minimize needle length.

This sequence of travels and bearings simplifies the movement of the needle tip to puncture point 3' of FIG. 2 and to path N of FIG. 5. Unlike arc system guides, the articulating arm configuration gives less interference to the surgeon and to the CT equipment, while retaining full approach flexibility. Note, bearing 14 can be located on the lower end of travel 8 and next to bearing 15 to achieve similar approaches. The adjustability of alignment, and portable floor mount enable the unit to be moved from CT table to operating table easily. Parallel needle paths are easily set up by fixing the bearing settings of 15, 14, and 13 and simply moving the bars 9, 11, and 8 (or 7) by discrete x, z, and y amounts, respectively.

The instrument of FIG. 6 is just one of many specific translation and rotation devices which can set up mechanically the calculated path. Other designs which are fixed to the patient or the CT device can be used to accomplish the same thing, and are included within the present invention. Various permutations of x, y, z, angle movement elements in series on the arm also are included within the scope of the invention.

Since many of the internal abdominal organs move with respiration, it can be required that the stereotaxic method for the body take respiratory motion into account. A respiratory gating device similar to the device described by Jones for use with chest CT: (Jones, K. R., A respiratory monitor for use with CT body scanning and other imaging techniques. BRF 55, 530–533 and Robinson P. and Jones K., Improved control of respiration during computed tomography by feedback monitoring), can be utilized. At the present time there is no known published literature on the use of a respiratory gating device for CT guided biopsies. The device employs a water in tube strain gauge that is strapped around the patient's chest which is connected to a transducer that will in turn give a digital readout as to the patient's phase of respiration. In this way, all scans can be taken in the same phase of inspiration.

Figure 7:
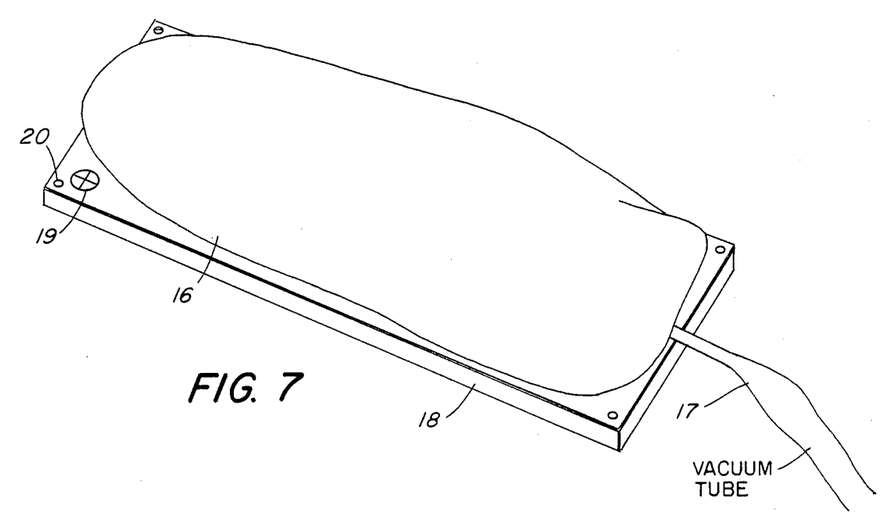
FIG. 7 illustrates in perspective a patient stablization board upon which the patient lies and integrated with the board is a strap that extends around the patient's chest for positioning a respiratory gating device.

In one possible configuration, the respiratory gating device, which can be strapped around the patient's chest, is anchored to the patient immobilization device. As shown in FIG. 7, the immobilizer comprises a plastic bag 16 which is filled with foam pellets. A tube 17, which is connected to the bag, is hooked up to wall suction which is activated after the patient has laid down on the bag. The air is then evacuated from the bag which becomes a rigid cast of the patient's body. Devices such as this are available commercially for immobilization for other x-ray procedures. There is no known published literature at the present time that indicates a device such as this has ever been used in connection with CT scanning or with CT guided biopsies. In fact, the commercially available bags are all too wide to fit into the aperture of the CT scanner.

Figures 8A, 8B, 9A, 9B, 9C:
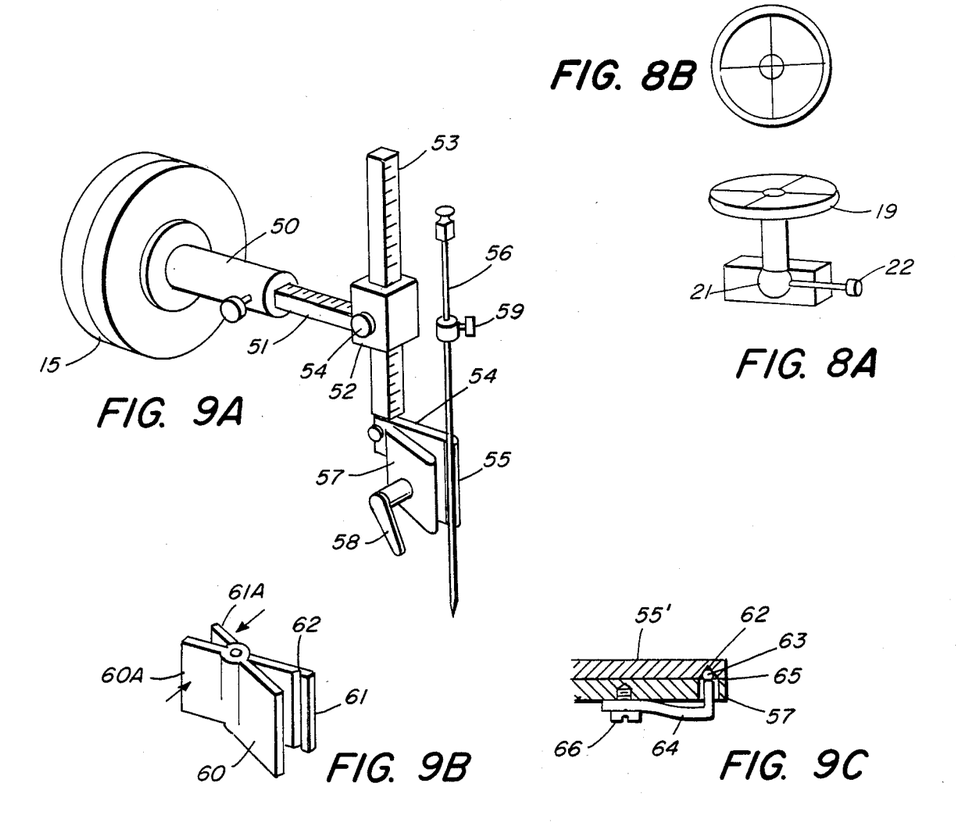

The foam filled bag, which is shown in FIG. 7, in turn anchored to a rigid board marked 18 on FIG. 7. The rigid board has a circular level 19 in one corner and adjustable corner posts 20 which can change the angulation of the support board. The circular level seen in FIG. 8 can rotate on a ball joint 21. When the bubble is centered, the ball joint is locked with a set screw 22. If this level is set while the patient is still on the CT table, the patient, while still on the immobilization device, can be moved to a different room for the biopsy. The patient can then be oriented to the stereotaxic frame using the localization device as a reference and, using the circular level, the patient can be oriented in space exactly as the CT scan was obtained. A similar function can be accomplished by multiple linear levels or other leveling device schemes.

FIG. 9 shows embodiments of two of many schemes for a quick-release needle guide system, analogous to 44, 43, and 12 in FIG. 6. In FIG. 9A, bearing 15 corresponds to that of FIG. 6, and is the declination bearing on the end of the articulating arm of the entire guide. Onto 15 is fastened a holder 50, into which slides metered bar 51. Set 52 clamps 51 at a given extension out of 50. Block 52 guides vertical bar 53, with scales on it too, and set screw 54 enables clamping of the two pieces. On the end of 53 is needle guide plate 54 with groove 55 to guide a needle 56. Plate 57 articulates on 54 to close and trap 56 into 55, providing sure directionality. Lever 58 enables quick opening of 57 relative to 54, so that needles can be put in or out quickly. The scale on 53 enables easy sighting on a depth stop 59 on 56 for determining depth of penetration. FIG. 9B shows another needle clip, possible instead of 57 and 54. This has two jaws 60 and 61 which open or close by pressing 60A and 61A, with groove 62 to guide a needle. Thus either lever, screw, twist lock, bobby-pin type, squeeze tab, or other type actuators are possible to enable a quick-release type needle guide, and all of these styles are intended to be included in this invention. It is noted that 55 and 57 or 60 and 61 may be spring loaded so that they tend to close or open depending on design. This can make easier the control of the device. Note too that upon inserting a needle in an upper right hand corner of an array on the skin, rows of needles down or to the left can be placed sequentially without interference of the guide shown in FIG. 9A. Thus a large array of parallel needles may be placed quickly wiht such an invention. Once a needle is guided into the body, 54 can be unlocked and 55 and 57 opened, and the slide bar 51 pushed to the left into 50 to clear the guide from the needle shaft 56. Then the guide can be set up to new settings, and the next needle inserted. In FIG. 9C, a V-groove type needle guide is shown with friction hold. V groove 62 in plate 55' gives sure guidance of needle shaft 63, and plate 57' gives clearance for 63. Spring 64 has tab end 65 that presses on 63 to hold it from slipping, yet allows easy travel when pushed. Screw 66 holds 64 in place on 57'.

Having described in detail various embodiments of our invention, it will now become apparent to those skilled in the art that many modifications can be made therein without departing from the scope of the invention as defined in the following claims.

What we claim and desire to secure by Letters of Patent of the United States are:

1. A method for determining a target point within a human body by means of tomographic cut images from a tomographic scanner comprising the steps of:
    (a) placing a localizer in a fixed position relative to the body and with at least a portion of said localizer being adjacent to the skin of the body such that a tomographic scan cut through said localizer will give a first image point location on the scan image which determines a first physical point on the patient's skin adjacent to said localizer;
    (b) taking a first tomographic cut through the body and through said localizer from which said first physical point on the skin can be determined and from which a second image point on the skin can be determined on the image of said first tomographic cut, whereby the coordinate differences between said first image point and said second image point enable the unique position of the associated second physical point on the patient's skin to be determined;
    (c) taking a second tomographic cut through the body with a known displacement distance from said first tomographic cut from which a target image point can be identified and from which the coordinate position of the associated physical target point in the body can be determined relative to said second physical point seen in said first tomographic cut; and,
    (d) calculating a trajectory in space relative to the planes of the tomographic cuts which passes through said second physical point on the skin and through said physical target point and calculating the distance along said trajectory between said physical point and said physical target point.

2. The method of claim 1 wherein said first image point coincides with said second image point, and correspondingly, said first physical point coincides with said second physical point in the body.

3. The method of claim 1 and further comprising the step of immobilizing the body by means of a flexible bag-like enclosure which can be partially filled with small, nearly incompressible objects, and which can be evacuated of air inside it and can be laid on a firm table means, whereby said immobilization step includes laying the body to be scanned on said bag-like enclosure which is on said firm table means, and evacuating said bag-like enclosure of air so that said bag-like enclosure takes the form of the body contacting it, thereby tending to fix the body's confirguration.

4. A method for directing an instrument into the human body to reach a target point within the body by means of tomographic cut images from a tomographic scanner comprising the steps of:
    (a) placing a localizer in a fixed position relative to the body and with at least a portion of said localizer being adjacent to the skin of the body such that a tomographic scan cut through said localizer will give a first image point location on the scan image which determines a first physical point on the patient's skin adjacent to said localizer;
    (b) taking a first tomographic cut through the body and through said localizer from which said first physical point on the skin can be determined and from which a second image point on the skin can be determined on the image of said first tomographic cut, whereby the coordinate differences between said first image point and said second image point enable the unique position of the associated second physical point on the patient's skin to be determined;
    (c) taking a second tomographic cut through the body with a known displacement distance from said first tomographic cut from which a target image point can be identified and from which the coordinate position of the associated physical target point in the body can be determined relative to said second physical point seen in said first tomographic cut; and, (d) calculating a trajectory in space relative to the planes of the tomographic cuts which passes through said second physical point on the skin and through said physical target point and calculating the distance along said trajectory between said second physical point and said physical target point;

(e) using a stereotaxic guidance apparatus means to guide said instrument along said calculated trajectory, such that said instrument will pass through the skin at said second physical point and reach said physical target point.

5. The method of claim 4 and further comprising the step of gating said step of guiding said instrument into said body with level of respiration by means of a respiratory gating device, which can detect the degree of expansion of the patient's body relative to respiratory action and which provides a readout means of said degree of expansion so that the patient or surgeon can determine identical degrees of respiration action, said gating step consisting of using said respiratory gating device to make equivalent the degree of respiration at said steps of taking said first and said second tomographic scan cuts and said step of guiding said instrument into the body with said stereotaxic apparatus.

6. The method of claim 4 further comprising the step of establishing a predefined set of three orthogonal axes relative to said scanning machine with a z-axis which is perpendicular to the axial tomographic cut image planes and essentially parallel to the longitudinal axis of a living body placed in said scanning machine, an x-axis which is substantially in a horizontal plane and which is substantially perpendicular to the direction of gravity, and a y-axis which is substantially in a vertical direction which is substantially parallel to the direction of gravity, said stereotaxic guidance apparatus comprising:

(i) a fixation means which is adapted to be placed in a fixed position relative to said scanning machine;

(ii) a probe carrier means which is adapted to carry said instrument as it is being directed into the living body;

(iii) an articulating arm means which connects between said fixation means and said probe carrier means, said articulating arm means comprising at least one x-bar which enables movement of said probe carrier means along said x-axis, at least one y-bar which enables movement of said carrier along said y-axis, at least one z-bar which enables movement of said probe carrier means along said z-axis, an azimuth rotation means part of said articulating arms means which enables rotation of said probe carrier means about said y-axis, and a declination rotation means part of said articulating arm means which enables rotation of said probe carrier means about an axis which is perpendicular to said y-axis; and further comprising the steps of:

(a) placing said instrument in said probe carrier means so it is being guided by said probe carrier means;

(b) adjusting said azimuth rotation means and said declination rotation means to positions so that the direction of said instrument corresponds to said calculated trajectory;

(c) moving said x-bar, y-bar, and z-bars so that the tip end of said instrument is at said second physical point on the patient's skin.

(d) pushing said instrument into the living body an amount equal to said calculated trajectory distance, so that said instrument tip end reaches said physical target point.

7. The method of claim 8 wherein said first image point coincides with said second image point, and correspondingly, said first physical point coincides with said second physical point in the body.

8. A method for determining a target point within a human body by means of tomographic cut images from a tomographic scanner comprising the steps of:

(a) placing a localizer in a fixed position relative to the body and with at least a portion of said localizer being adjacent to the skin of the body such that a tomographic scan cut through said localizer will give a first image point location on the scan image which determines a first physical point on the patient's skin adjacent to said localizer;

(b) taking at least one tomographic cut through the body and through said localizer from which said first physical point on the skin can be determined and from which a second image point on the skin can be determined on the image of said at least one tomographic cut, whereby the coordinate differences between said first image point and said second image point enable the unique position of the associated second physical point on the patient's skin to be determined;

(c) identifying a target image point on the image of said at least one tomographic cut and from which the coordinate position of the associated physical target point in the body can be determined relative to said second phusical point seen in said at least one tomographic cut; and, (d) calculating a trajectory in space relative to the plane of said at least one tomographic cut which passes through said second physical point on the skin and through said physical target point and calculating the distance along said trajectory between said physical point and said physical target point.

9. The method of claim 8 wherein said localizer comprises a triangular means that can be placed on the body during tomographic scanning and which has a base side that can be aligned parallel to the scan plane prior to scanning, with a section of said triangular means being visible on a tomographic cut through it so that the edges of the triangle means sides can be identified in order that said first image and first physical points can be determined relative to said edges, and further comprising the step of making said at least one tomographic cut with said triangular means positioned on the body so as to determine said first physical point.

10. The method of claim 8 wherein said localizer comprises a triangular means having at least a portion of its interior area free of material so that it can lay on a curved portion of the body's surface with its edges in close proximity to the body's skin during tomographic scanning and which has a base side that can be aligned parallel to the scan plane prior to scanning with a section of said triangular means being visible on a tomographic cut through it so that the edges of the triangle means sides can be identified in order that said first image and first physical points can be determined relative to said edges, and further comprising the steps of positioning said triangular means on a curved portion of the body and then making said at least one tomographic cut with said triangular means positioned on the curved portion of the body so as to determine said first physical point.

11. The method of claim 8 wherein said localizer comprises a triangular means having lines on it parallel to said base edge and located such that they correspond to integral unit distances across said triangular means from one of its said side edges to another and further comprising the step of determining from said at least one tomographic cut the distance across said triangular means whereby said lines on said triangular means locate said first physical point.

12. A method for directing an instrument into the human body to reach a target point within the body by means of tomographic cut images from a tomograhic scanner comprising the steps of:
   (a) placing a localizer in a fixed position relative to the body and with at least a portion of said localizer being adjacent to the skin of the body such that a tomographic scan cut through said localizer will give a first image point location on the scan image which determines a first physical point on the patient's skin adjacent to said localizer;
   (b) taking at least one tomographic cut through the body and through said localizer from which said first physical point on the skin can be determined and from which a second image point on the skin can be determined on the image of said at least one tomographic cut, whereby the coordinate differences between said first image point and said second image point enable the unique position of the associated second physical point on the patient's skin to be determined;
   (c) identifying a target image point on the image of said at least one tomographic cut and from which the coordinate position of the associated physical target point in the body can be determined relative to said second physical point seen in said at least one tomographic cut;
   (d) calculating a trajectory in space relative to the plane of said at least one tomographic cut which passes through said second physical point on the skin and through said physical target point and calculating the distance along said trajectory between said physical point and said physical target point; and,
   (e) using a stereotaxic guidance apparatus means to guide said instrument along said calculated trajectory, such that said instrument will pass through the skin at said second physical point and reach said physical target point.

* * * * *